United States Patent
Whittaker

(10) Patent No.: US 9,513,241 B2
(45) Date of Patent: Dec. 6, 2016

(54) SYSTEMS AND METHODS FOR INTERPRETING MULTI-PHASE FLUID FLOW DATA

(75) Inventor: Andrew Colin Whittaker, Phuket (TH)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1300 days.

(21) Appl. No.: 13/310,786

(22) Filed: Dec. 4, 2011

(65) Prior Publication Data

US 2012/0166108 A1 Jun. 28, 2012

Related U.S. Application Data

(60) Provisional application No. 61/426,625, filed on Dec. 23, 2010, provisional application No. 61/426,640, filed on Dec. 23, 2010, provisional application No. 61/447,174, filed on Feb. 28, 2011.

(51) Int. Cl.
| | |
|---|---|
| G06F 19/00 | (2011.01) |
| G01N 25/60 | (2006.01) |
| E21B 43/24 | (2006.01) |
| E21B 47/00 | (2012.01) |

(52) U.S. Cl.
CPC ............... *G01N 25/60* (2013.01); *E21B 43/24* (2013.01); *E21B 47/00* (2013.01)

(58) Field of Classification Search
USPC .......................................................... 702/45
See application file for complete search history.

(56) References Cited

U.S. PATENT DOCUMENTS

| | | | |
|---|---|---|---|
| 3,965,980 A | | 6/1976 | Williamson |
| 4,681,466 A | | 7/1987 | Chien et al. |
| 4,753,106 A | | 6/1988 | Brenner et al. |
| 4,817,713 A | | 4/1989 | Nguyen et al. |
| 4,836,032 A | | 6/1989 | Redus et al. |
| 5,061,377 A | | 10/1991 | Lee et al. |
| 5,094,103 A | | 3/1992 | Wicks, III et al. |
| 5,138,876 A | | 8/1992 | Moore et al. |
| 5,331,284 A | | 7/1994 | Jean et al. |
| 5,361,206 A | | 11/1994 | Tabeling et al. |
| 5,509,478 A | | 4/1996 | Stoy |
| 5,661,237 A | | 8/1997 | Dussan et al. |
| 5,831,743 A | | 11/1998 | Ramos et al. |
| 5,949,069 A | * | 9/1999 | Chace ................. E21B 47/1015 250/256 |
| 6,023,340 A | | 2/2000 | Wu et al. |
| 6,216,532 B1 | | 4/2001 | Stephenson et al. |
| 6,389,367 B1 | | 5/2002 | Plasek |
| 6,629,564 B1 | | 10/2003 | Ramakrishnan et al. |
| 6,776,054 B1 | | 8/2004 | Stephenson et al. |
| RE38,642 E | | 11/2004 | Gondouin |

(Continued)

OTHER PUBLICATIONS

Xie C.G., et al., "Imaging technologies in oilfield applications," Journal of Zhejiang Universigy Science A., vol. 6A, No. 12, Dec. 1, 2005, pp. 1394-1400.

(Continued)

*Primary Examiner* — Edward Raymond
(74) *Attorney, Agent, or Firm* — Michael Dae

(57) ABSTRACT

Methods and systems are disclosed for interpreting multi-phase fluid flow in a conduit, such as a pipe in a wellbore. The method involves curve fitting holdup data sets and velocity data sets together wherein the second curve comprises a shape mutual to the first curve with an independent gain and an independent offset, and determining flow rates through the pipe.

23 Claims, 11 Drawing Sheets

(56) References Cited

U.S. PATENT DOCUMENTS

| | | | |
|---|---|---|---|
| 6,873,267 | B1 | 3/2005 | Tubel et al. |
| 6,959,140 | B2 | 10/2005 | Cens et al. |
| 7,062,420 | B2 | 6/2006 | Poe, Jr. |
| 7,099,780 | B2 | 8/2006 | Faur et al. |
| 7,114,386 | B1 | 10/2006 | Veignat et al. |
| 7,231,835 | B2 | 6/2007 | Dutton et al. |
| 7,301,609 | B2 | 11/2007 | Cens et al. |
| 7,324,924 | B2 | 1/2008 | Barajas et al. |
| 7,351,034 | B2 | 4/2008 | Cens et al. |
| 7,406,883 | B2 | 8/2008 | Faur et al. |
| 7,603,236 | B2 | 10/2009 | North et al. |
| 2001/0000060 | A1 | 3/2001 | Toma et al. |
| 2005/0229718 | A1 | 10/2005 | Cens et al. |
| 2006/0041382 | A1* | 2/2006 | Faur .................. G01F 1/74 702/6 |
| 2007/0179753 | A1* | 8/2007 | Barajas ............ G05B 19/4183 702/189 |
| 2008/0046186 | A1 | 2/2008 | North et al. |
| 2008/0065362 | A1 | 3/2008 | Lee et al. |
| 2008/0208429 | A1 | 8/2008 | Saravanapriyan et al. |
| 2008/0231860 | A1 | 9/2008 | Melnyk |
| 2009/0308601 | A1 | 12/2009 | Poe, Jr. et al. |
| 2010/0147066 | A1 | 6/2010 | Ziauddin |
| 2010/0155060 | A1 | 6/2010 | Hanna |
| 2011/0139442 | A1 | 6/2011 | Ziauddin et al. |
| 2012/0166108 | A1 | 6/2012 | Whittaker |

OTHER PUBLICATIONS

Gerald Catala, et al., "Fluid Flow Fundamentals", Oilfield Review—Schlumberger, vol. 8, No. 4.

International Search Report for the equivalent PCT patent application No. PCT/IB11/055687 issued on Jun. 13, 2012.

Communication ursuant to Article 94 (3) issued in the related EP Application 11808356.07, dated Jul. 18, 2014, 3 pages.

Communication ursuant to Article 94 (3) issued in the related EP Application 11808356.07, dated Jun. 29, 2015, 3 pages.

International Preliminary Report on Patentability issued in the related PCT application PCT/IB2011/055686, dated Jun. 25, 2013, 5 pages.

International Search Report and Written Opinion issued in the related PCT application PCT/IB2011/055686, dated Mar. 29, 2012, 7 pages.

International Preliminary Report on Patentability issued in the related PCT application PCT/IB2011/055687, dated Jun. 25, 2013, 10 pages.

International Search Report and Written Opinion issued in the related PCT application PCT/IB2011/055687, dated Jun. 13, 2012, 16 pages.

International Preliminary Report on Patentability issued in the related PCT application PCT/IB2011/055688, dated Jun. 25, 2013, 6 pages.

International Search Report and Written Opinion issued in the related PCT application PCT/IB2011/055688, dated Jun. 8, 2012, 12 pages.

American Gas Association "Measurement of Natural Gas by Turbine Meters" Aga Report No. 7 (2006) 11 pages.

Husch, Lawrence "Average Value of a Function" Wayback Machine Web archive (Mar. 2009) available at http://web.archive.org/web/20090330194909/http://archives.math.utk.edue/visual.calculas/5/average.1/, 1 page.

John Baldauff, et al., Profiling and Quantifying Complex Multiphase Flow, Oilfield review, Oct. 1, 2004, pp. 4-13.

Gorham, John "Fundamental Principles of Gas Turbine Meters" (2007), 6 pages.

R. Krishna, et al., "Three-Phase Eulerian simulations of bubble column reactors operating in the churn-turbulent regime: a scale up strategy", Chemical Engineering Science, vol. 55, No. 16 XP 55028293, 12 pages.

Schlumberger "Glossary: Flowmeter" available from http://www.glossaiy.oilfield.slb.com/en/terms/f/flowmeter.aspx? p=1, 1 page.

Sondex Spinner Selection Guide, Dec. 20, 2007, pp. 1-6.

Wagner and Kretzschmar, International Steam Tables—Properties of Water and Steam based on the Industrial Formulation IAPWS-IF97, 2008, 2nd Ed., pp. 8, 13 and 14.

Huang Ming-Chih, et al. "The Pre-Processing of Data Points for curve fitting in reverse engineering", The international Journal of Advanced manufacturing technology, vol. 40, Issue 13, 1913-1927, Year Oct. 2000, pp. 635-642.

* cited by examiner

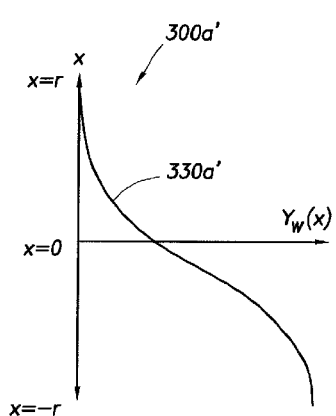 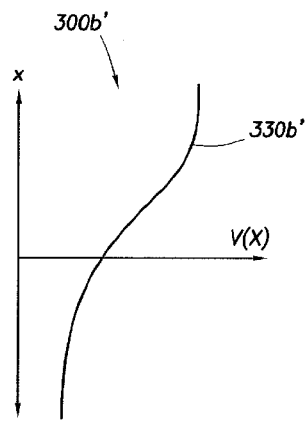 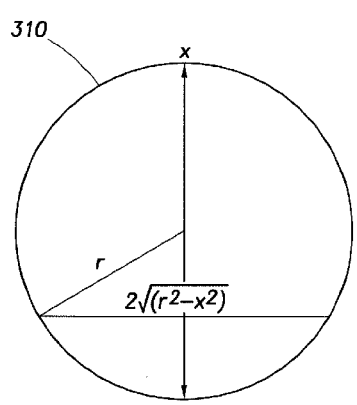
FIG.3-4    FIG.3-5    FIG.3-6

SYSTEMS AND METHODS FOR INTERPRETING MULTI-PHASE FLUID FLOW DATA

CROSS-REFERENCE TO RELATED APPLICATIONS

This application claims the benefit of U.S. Provisional Application No. 61/426,640, filed Dec. 23, 2010, U.S. Provisional Application No. 61/426,625, filed Dec. 23, 2010, and U.S. Provisional Application No. 61/447,174, filed Feb. 28, 2011, the entire disclosure of each application is incorporated herein by reference.

This application relates to U.S. Application titled "APPARATUS AND METHOD FOR GENERATING STEAM QUALITY DELIVERED TO A RESERVOIR" and filed Dec. 4, 2011 with Ser. No. 13/310,785 and U.S. Application titled "METHODS AND SYSTEMS FOR INTERPRETING MULTIPHASE FLUID FLOW IN A CONDUIT" and filed Dec. 4, 2011 with Ser. No. 13/310,788, the entire disclosure of each application is incorporated herein by reference.

BACKGROUND

Multi-phase fluid flow may have at least two phases: a fluid phase (e.g. oil phase) and a vapor phase (e.g. gas). In some cases, a multi-phase fluid flow may have three phases: a heavy fluid phase (e.g. aqueous phase), a light fluid phase (e.g. oil phase) and a vapor phase. Multi-phase fluid flow in a conduit can be encountered in industries, such as petrochemical plants, oil/gas production fields, and food stuff processing plants. It may be useful to measure and interpret characteristics of multi-phase fluid flow.

Multi-phase fluid flows may be encountered in the oil/gas production industry. In an oil/gas production context, various flow regimes reflective of various multi-phase fluid flows may be found, such as stratified flow, wavy stratified flow, plug flow, slug flow, dispersed bubble flow, and annular flow. Annular flow refers to gas flowing at high velocities in a center of a borehole with a fluid confined to a thin film on walls of the borehole. Stratified flow can occur in horizontal wells when two or more phases are separated due to gravity. Wavy flow can result in stratified systems when interference occurs between the two phases traveling at different velocities.

Factors influencing the flow regimes can include a degree of borehole deviation and proportion of each phase; relative differences in phase densities, surface tension and viscosity of each phase; and average velocity. In a fluid-gas system, when small bubbles of gas are uniformly distributed, the flow regime can be referred to as dispersed bubble flow. When some of these bubbles aggregate to form larger bubbles, plug flow and slug flow can result.

Understanding the multi-phase fluid flow regime in a conduit or pipe may be used to understand how a production well is performing. A production log records one or more in-situ measurements that describe the nature and behavior of fluids in or around the borehole during a production operation, including an injection operation. Production logs can provide, for example, information about dynamic well performance, and the productivity or infectivity of different zones. This information may be used to help diagnose problem wells, or monitor the results of a stimulation or completion.

Various downhole tools can be used for making downhole measurements used to produce logs, including flowmeters (e.g., spinners), local probes, nuclear logging tools, phase-velocity logging tools, production logging sensors, etc. Downhole tools may be used to measure various downhole parameters, such as temperature, flow rate, density, phase velocity, phase holdup, mixture density, mixture velocity, water (or liquid) holdup, water velocity, gas holdup, and the like.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

This summary is provided to introduce a selection of concepts that are further described below in the detailed description. This summary is not intended to identify key or essential features of the claimed subject matter, nor is it intended to be used as an aid in limiting the scope of the claimed subject matter.

The techniques herein relate to methods and systems for interpreting measurements of a multi-phase fluid flow in a conduit. The methods involve obtaining holdup and velocity measurements using, for example a downhole logging tool. The method can include fitting first and second curves to the holdup measurements and the velocity measurements. The curves have a shape mutual to the first curve with an independent gain and an independent offset.

The disclosure relates to a method for interpreting measurements of a multi-phase fluid flow in a conduit. The method involves obtaining a set of holdup measurements, obtaining a set of velocity measurements, fitting a first curve to a first set of one of the set of holdup measurements and the set of velocity measurements, and fitting a second curve to a second set of one of the set of holdup measurements and the set of velocity measurements, wherein the second curve comprises a shape mutual to the first curve with an independent gain and an independent offset.

The first set may be the set of holdup measurements and the second set is the set of velocity measurements, and the first curve may be a holdup profile and the second curve is a velocity profile. The first curve may include one of a function with a linear fit to the set of holdup measurements and the set of velocity measurements; a function with spline interpolations; and a function with spline interpolations and a constant projection. The first curve may include a hyperbolic tangent curve with at least two adjustable curve-fitting coefficients.

The method may further involve modifying the first or second curve that is fitted to the set of velocity measurements according to Prandtl's law at a wall of the conduit, wherein the modified curve comprises a velocity profile. The method may also involve modifying the first or second curve that is fitted to the set of velocity measurements based on an averaging effect of the set of velocity measurements, wherein the modified curve is a modified velocity profile; and generating a fluid flow rate with a holdup profile and the modified velocity profile. The method may also involve generating a first curve-fitting error for the first curve, generating a second curve-fitting error for the second curve, generating a total curve-fitting error as a sum of the first and second curve-fitting errors, and rejecting the set of holdup measurements and the set of velocity measurements when the total curve-fitting error is above a threshold.

The method may also involve validating the set of holdup measurements and the set of velocity measurements when the total curve-fitting error is equal to or below the threshold; and adjusting at least one curve-fitting parameter of the first curve and the second curve to minimize the total curve-fitting error. The set of holdup measurements may be obtained from a holdup sensor, and the set of velocity measurements obtained from a velocity sensor. The method may also involve generating a fluid flow rate according to a holdup profile and a velocity profile. The conduit may be a pipe in an oilfield wellbore.

The disclosure also relates to a method for interpreting measurements of a multi-phase fluid flow in a conduit involving obtaining at least one fluid holdup measurement; obtaining a set of velocity measurements; fitting a first curve to the set of velocity measurements as the velocity profile; and using the first curve constrained by the at least one fluid holdup measurement to form a second curve as the fluid holdup profile. The fluid holdup measurement may be a pipe average holdup measurement or a local probe holdup measurement. The pipe average holdup measurement may be obtained from a pulsed-neutron gamma ray-energy discriminating logging tool.

The disclosure further relates to a method for interpreting measurements of a multi-phase fluid flow in a conduit involving obtaining at least one velocity measurement; obtaining a set of fluid holdup measurements, fitting a first curve to the set of fluid holdup measurements as the fluid holdup profile, and using the first curve constrained by the at least one velocity measurement to form a second curve as the velocity profile. The velocity measurement may be a pipe average velocity measurement or a local velocity measurement.

The disclosure also relates to a system for interpreting measurements of a multi-phase fluid flow in a conduit. The system includes a holdup sensor to obtain a set of fluid holdup measurements; a flow velocity sensor to obtain a set of velocity measurements; a processor in electronic communication with the holdup sensor and the flow velocity sensor, the processor fitting a first curve to one of the set of fluid holdup measurements and the set of velocity measurements and fitting a second curve to another one of the set of fluid holdup measurements and the set of velocity measurements, wherein the second curve has a same shape of the first curve with an independent gain and an independent offset and wherein the first curve and the second curve comprise a fluid holdup profile and a velocity profile.

The first curve may be a hyperbolic tangent curve with two adjustable curve-fitting coefficients. The holdup sensor and the flow velocity sensor may be disposed about a downhole tool configured to move inside the conduit. The processor may include a computer readable data storage in electronic communication with the processor that stores the set of fluid holdup measurements and the set of velocity measurements. The computer readable data storage may include computer executable instructions that, when executed by the processor, causes the processor to compute a fluid flow rate in the conduit; computer executable instructions that, when executed by the processor, causes the processor to constrain a fluid holdup profile by one measurement of the set of velocity measurements; computer executable instructions that, when executed by the processor, cause the processor to constrain a velocity profile by one measurement of the set of fluid holdup measurements; computer executable instructions that, when executed by the processor, cause the processor to: compute a total curve-fitting error as a function of a first curve-fitting error for the first curve and a second curve-fitting error for the second curve and reject the set of velocity measurements and the set of fluid holdup measurements when the total curve-fitting error exceeds a threshold.

BRIEF DESCRIPTION OF THE DRAWINGS

Embodiments of methods and apparatuses for interpreting multi-phase fluid flow data are described with reference to the following figures. Like numbers are used throughout the figures to reference like features and components.

FIGS. 3-1 through 3-3 are graphical illustrations depicting holdup data and velocity data for a cross-sectional area of pipe.

FIGS. 3-4 through 3-6 are graphical illustrations depicting holdup data and velocity data for another cross-sectional area of pipe.

FIGS. 4-1 through 4-3 are graphical illustrations depicting vertical pipe diameter as a function of holdup data, velocity data and a combination of holdup and velocity data.

FIG. 5-1 through 5-4 are schematic, graphical illustrations depicting curve fitting techniques using holdup and velocity data.

FIG. 6 is a flow diagram of an example method of interpreting measurements of a multi-phase fluid flow in a conduit.

DETAILED DESCRIPTION

In the following description, numerous details are set forth to provide an understanding of the present disclosure. However, it will be understood by those skilled in the art that the present disclosure may be practiced without these details and that numerous variations or modifications from the described embodiments are possible.

This disclosure describes methods and systems to interpret measurements of a multi-phase fluid flow in a conduit. The methods may involve interpreting measurements relating to a multi-phase fluid flow, e.g. production logging data. Techniques are described to fit curves with a mutual shape to velocity data and holdup data, the curves of mutual shape being similar apart from a gain and an offset. This disclosure also describes related methods for incorporating such data for interpretation, for example to generate flow rates from the holdup and phase velocities of the fluid.

With reference to multi-phase flow in pipes, holdup can be described as the fraction of a particular fluid present in an interval of pipe. In the multi-phase flow, each fluid may move at a different speed due to gravitational forces and other factors. Heavier phases may move more slowly, or may be more held up, than the lighter phase. Phase velocity can be described as the velocity with which a particular phase (gas, oil, or water) moves in a producing well.

For purposes of this disclosure, two functions may be considered the same or similar as long as they have their shape in common with one another. For computational efficiency, the two functions may be expressed in identical polynomials, or a particular function or a series of functions. The two functions are considered, for purposes herein, to be the same or similar as long as the error between them is not greater than curve fitting errors.

In the oil industry, a downhole tool (e.g., a production logging tool) may be used to obtain data about a well in an oilfield, including the fluid flow in the well. Understanding and using the data, in complex flow regimes, such as those found in deviated wells, for decision making regarding well operation can be difficult. An example embodiment using data from a downhole tool (e.g., a flow scanner logging tool) is provided, but data from any other downhole tool can be used as well in various other embodiments.

Figure 1:
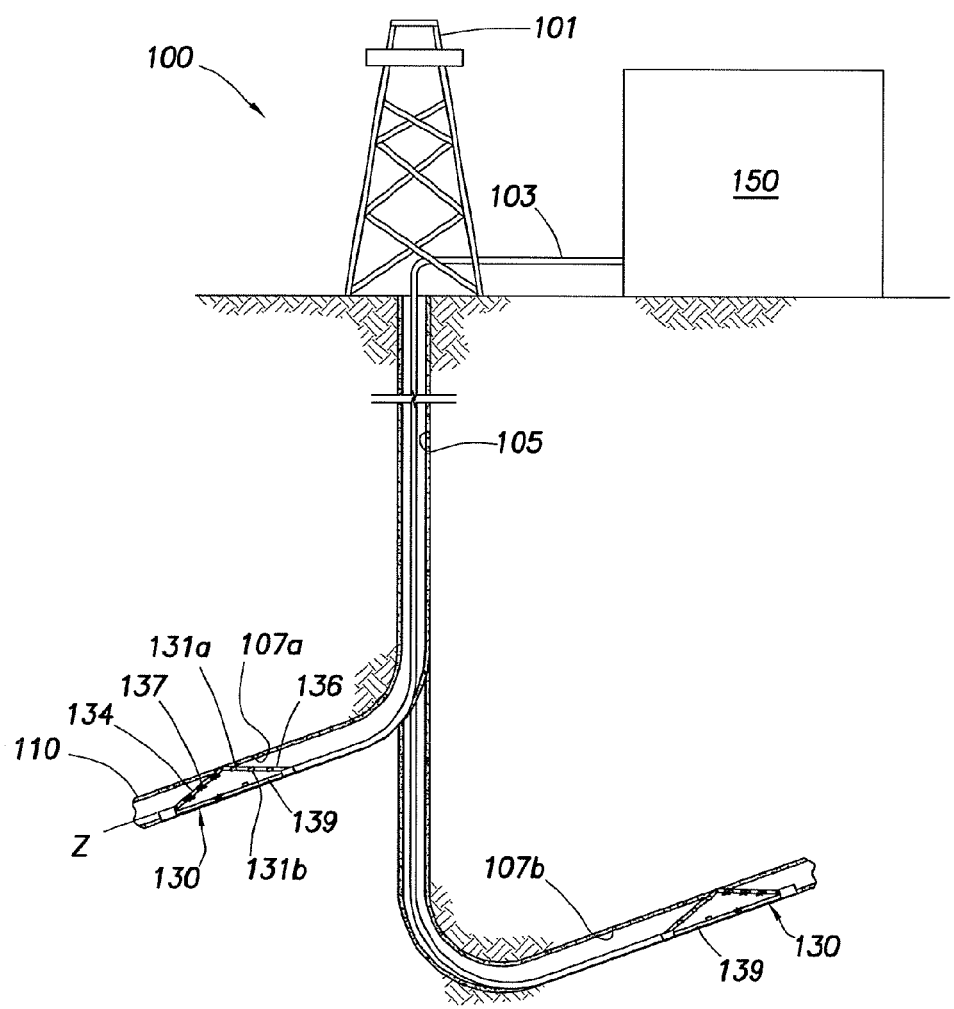
FIG. 1 is a schematic diagram showing an example of a wellsite system for a production well.

FIG. 1 depicts a wellsite 100 with a downhole tool (or production logging tool) 130 deployed into a wellbore 105 from a surface rig 101. As shown, the downhole tool 130 may be designed to be run on a low side of a pipe 110 in the wellbore 105 (low being the bottom of the pipe in a deviated or horizontal position relative to the surface). The downhole tool 130 may include two spring loaded arms 134, 136 with sensors mounted thereon for orienting the downhole tool 130 along a pipe axis Z.

Figure 2:
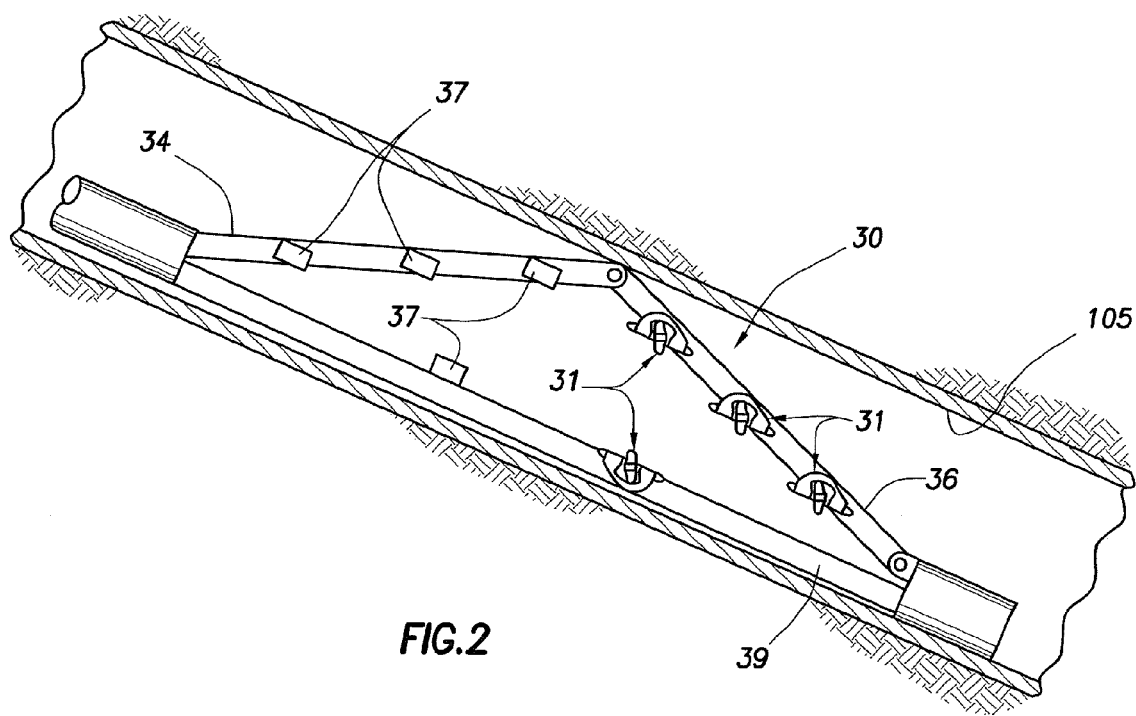
FIG. 2 is a schematic diagram of a production logging tool that may be used in the wellsite system of FIG. 1 to make measurements that can be used in accordance with various embodiments of the present disclosure.

FIG. 2 shows additional detail of a downhole tool 30 usable as the downhole tool 130 of FIG. 1 with three (3) mini-spinner flow meters (or mini-spinners) 37 on a leading arm 34, three holdup probes 31 on the trailing arm 36, one mini-spinner flow meter 37 and one holdup probe 31 on the tool 130 body 39. The mini-spinners 37 and holdup probes 31 may be used to acquire downhole data at various locations in the wellbore 105.

Referring back to FIG. 1, the leading arm 134 may include various sensors, such as four mini-spinners 137 mounted thereon, and the trailing arm 136 may include five water holdup probes 131a and five gas holdup probes 131b. Additional mini-spinners, water holdup probes, and gas holdup probes may optionally be mounted on the tool body 139. Measurements of a spring loaded arm caliper and tool relative bearing may be used to provide a physical location of each sensor to be determined within a circular cross section of the pipe. As would be recognized by one of skill in the art, any number of sensors (e.g., probes) for holdup and velocity measurements could be included in the downhole tool 130 in order to obtain a number of measurements adequate to support a flow rate determination.

A surface unit 150 may be in communication with the downhole tool 130 via a wireline 103 (or other telemetry device) for receiving the data acquired. Various computer systems and processors at either the surface unit 150 and/or downhole tool 130, or distributed between the two, may be used to interpret the data to determine, for example, the performance of the well.

In an example embodiment, the downhole data can be processed using various interpretation techniques, such as SCHLUMBERGER™'s OP FSI-IP™, BORFLOW™, or FSI²™; EMERAUDE™ commercially available from Kappa Petroleum Engineering Software Company; or other applicable software packages. Data may also be curve-fitted with various commercial packages, such as Schlumberger's MAPFLO™. Any number of curve-fitting algorithms may be employed, such as, for example, any non-linear least squares curve fitting like the Levenberg-Marquardt algorithm.

The downhole tool 130 of FIGS. 1 and 2 may be used in vertical or deviated wells (e.g., horizontal having a deviation of about ninety degrees, or angled at deviation of from about eighty to about one hundred degrees from vertical). When the axial direction of the well has a deviation of from about eighty to about ninety degrees as shown in portion 107a of wellbore 105, the flow in the well may be slightly uphill. On the other hand, when the axial direction of the well 105 has a deviation of about from about ninety to about one hundred degrees as shown in portion 107a of wellbore 105, the flow in the well is slightly downhill.

A holdup curve and a velocity curve may be derived from downhole data obtained as downhole tool scanner measurements are defined about the vertical axis of a horizontal pipe. From the two curves, a flow rate for the given phase (i.e., water if the water holdup and mixture velocity curves are used) can be generated. The flow rate can, in turn, be used to describe the multi-phase flow in the pipe.

Figures 1, 2, 3:
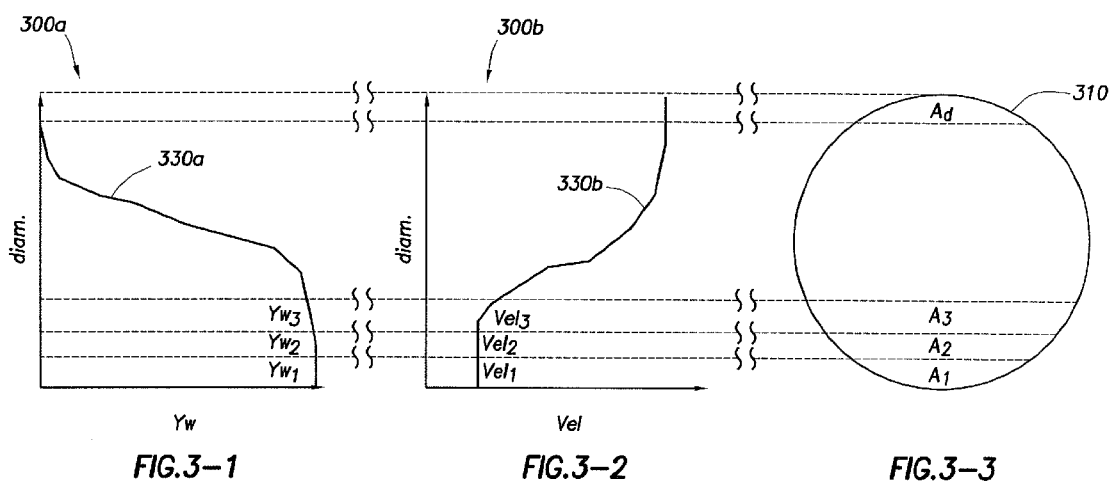

FIG. 3-1 is a chart 300a depicting a data set for a fluid holdup curve for a fluid phase of a multi-phase flow from the bottom to the top of a pipe 310. The chart 300a plots a holdup profile 330a based on pipe diameter (diam) (y-axis) versus water holdup (Yw) (x-axis). FIG. 3-2 is a chart 300b depicting a data set for a velocity profile 330b for the same pipe 310. The chart 300b plots the velocity profile 330b based on pipe diameter (diam) (y-axis) versus fluid velocity (Vel) (x-axis). The holdup profile 330a is approximately a mirror image of the velocity provide 330b.

FIG. 3-3 shows a cross-section of the pipe 310. The conduit for multi-phase flow discussed herein is assumed to be a cylindrical pipe 310, as shown in FIG. 3-3, but various other shapes may also be used. In multiphase flow, the various layers 1-$d$ of fluids in areas $A_{1-d}$ of the pipe 310 may each have different holdups $Yw_{1-3}$ velocities $Vel_{1-3}$. The fluid flow rate ($Q_w$) for a multiphase flow can be expressed according to the function (assuming no slip between the layers):

$$Q_w = \sum_{n=1}^{n=d} Yw_n Vel_n A_n, \qquad \text{Eq. 1}$$

where $Q_w$ is the water flow rate; $Yw_n$ is the water holdup for the n'th layer; $Vel_n$ is the average velocity for the n'th layer; and $A_n$ is the cross-section area for the n'th layer. With the addition of slip, the multiphase flow can be expressed according to the function:

$$Q_w = \sum_{n=1}^{n=d} Yw_n (Vel_n - Vs_n(1 - Yw_n)) A_n, \qquad \text{Eq. 2}$$

where $Vs_n$ is the slip velocity for the n'th layer.

The multiphase flow rate ($Q_w$) may be computed (assuming that the holdup profile and velocity profile are properly measured). To accommodate for profiling to deal with various potential errors (e.g., sensor inaccuracy, sensor damage or inappropriate sensor position), curve fitting may be applied to both the holdup data and velocity data (e.g., using the interpretation techniques described above).

Figures 1, 4:
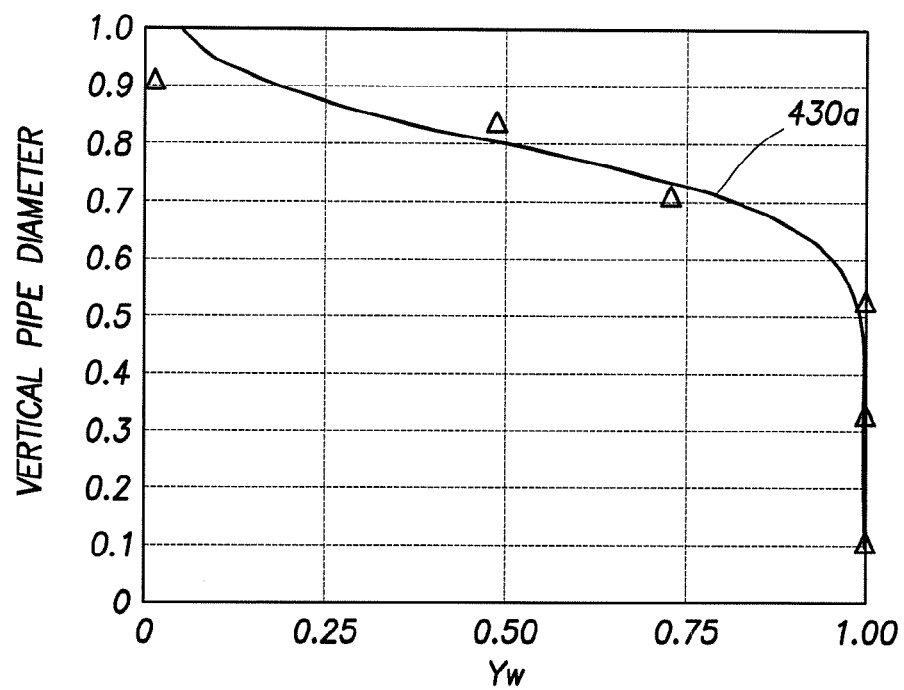
Figures 2, 4:
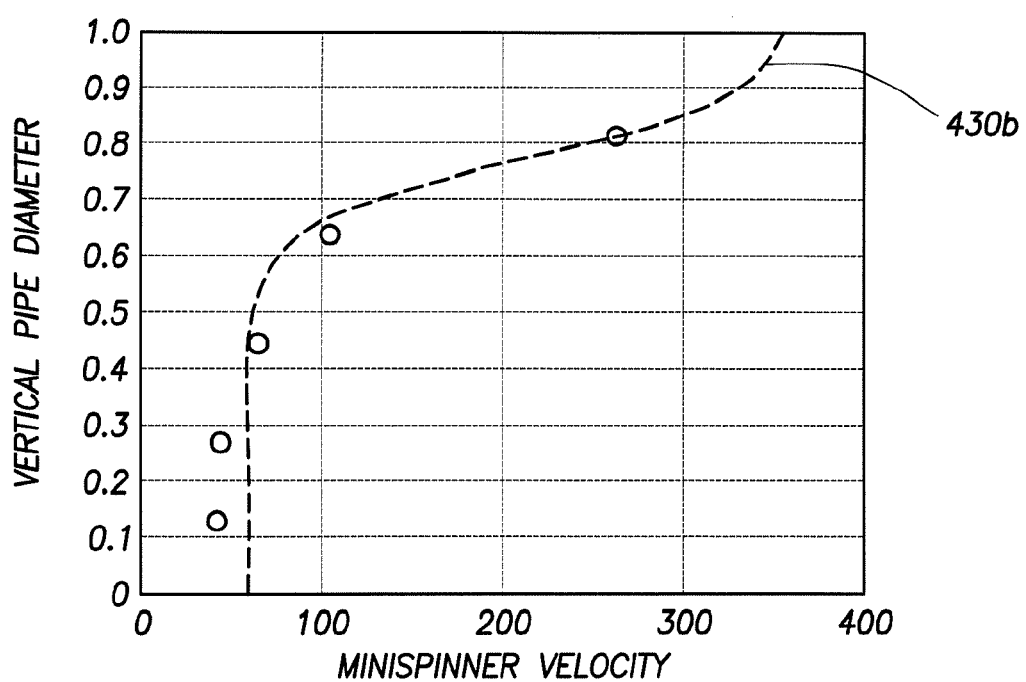
Figures 3, 4:
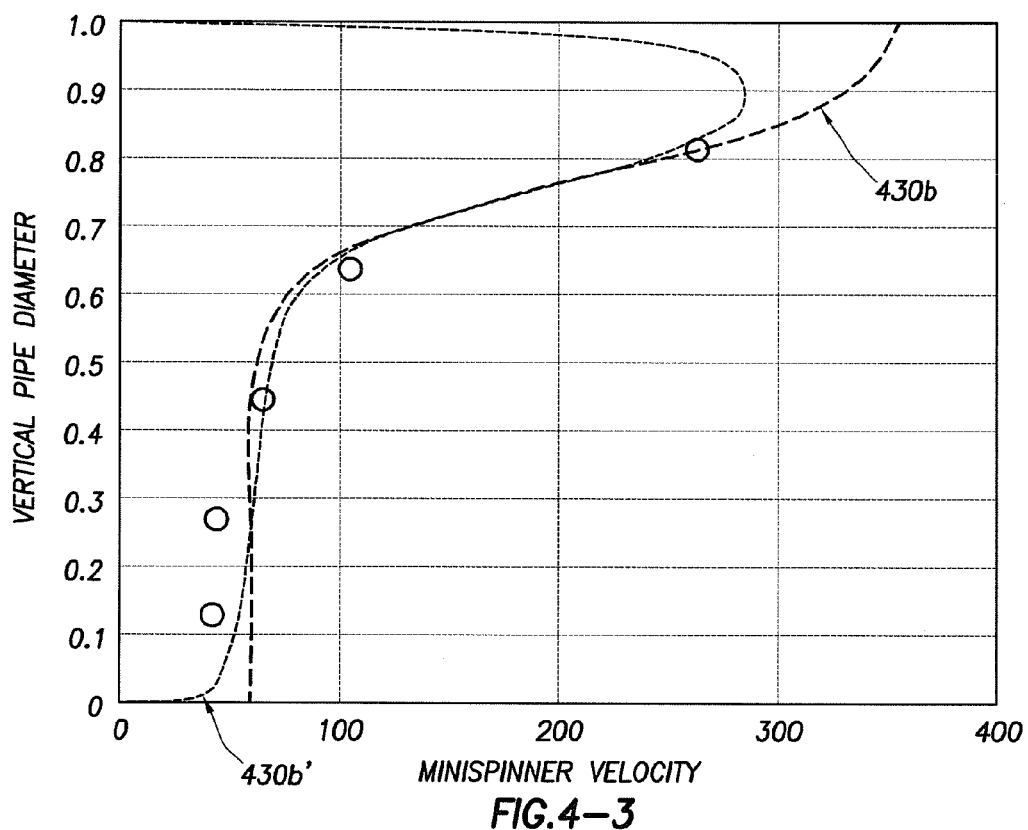
Figures 1, 5:
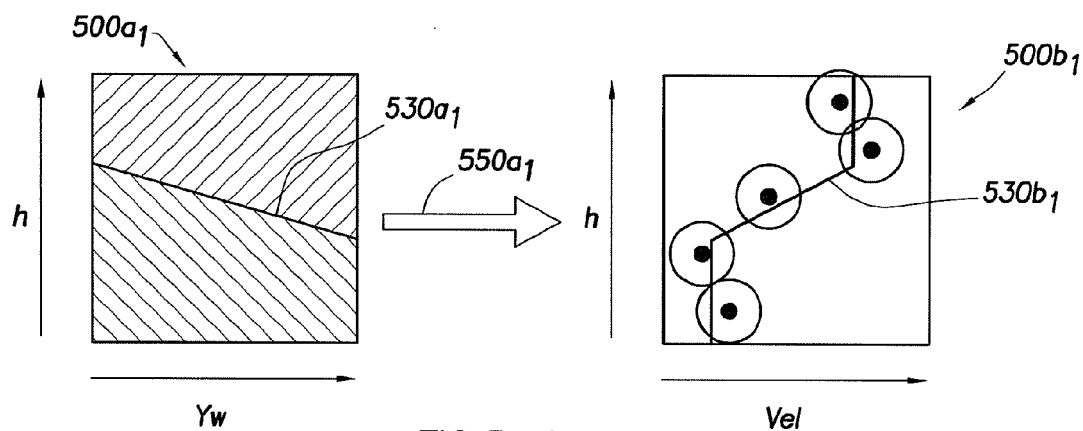
Figures 2, 5:
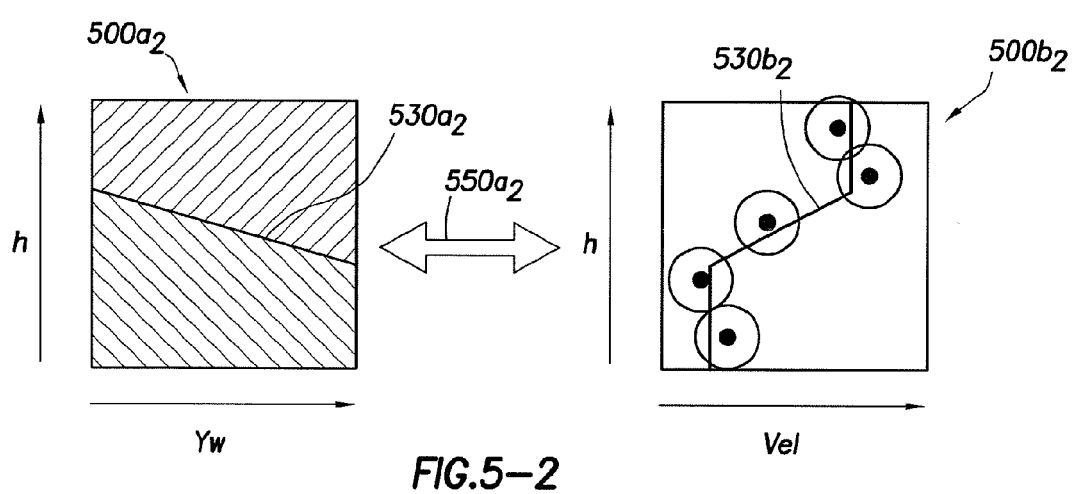
Figures 3, 5:
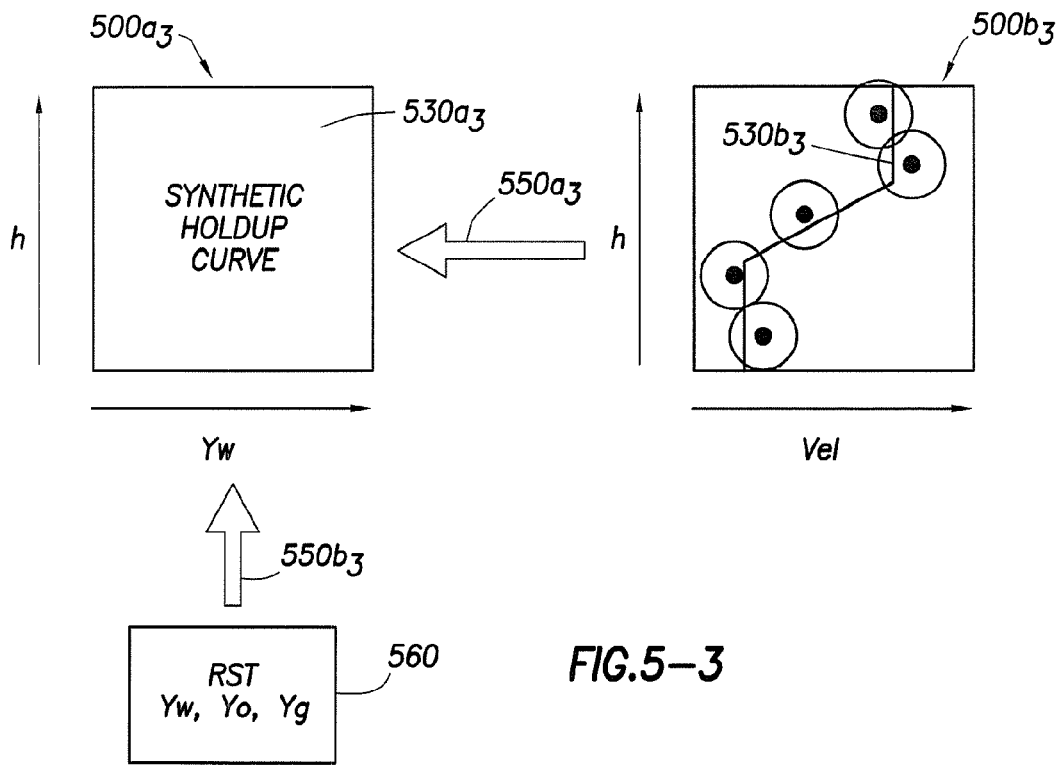
Figures 4, 5:
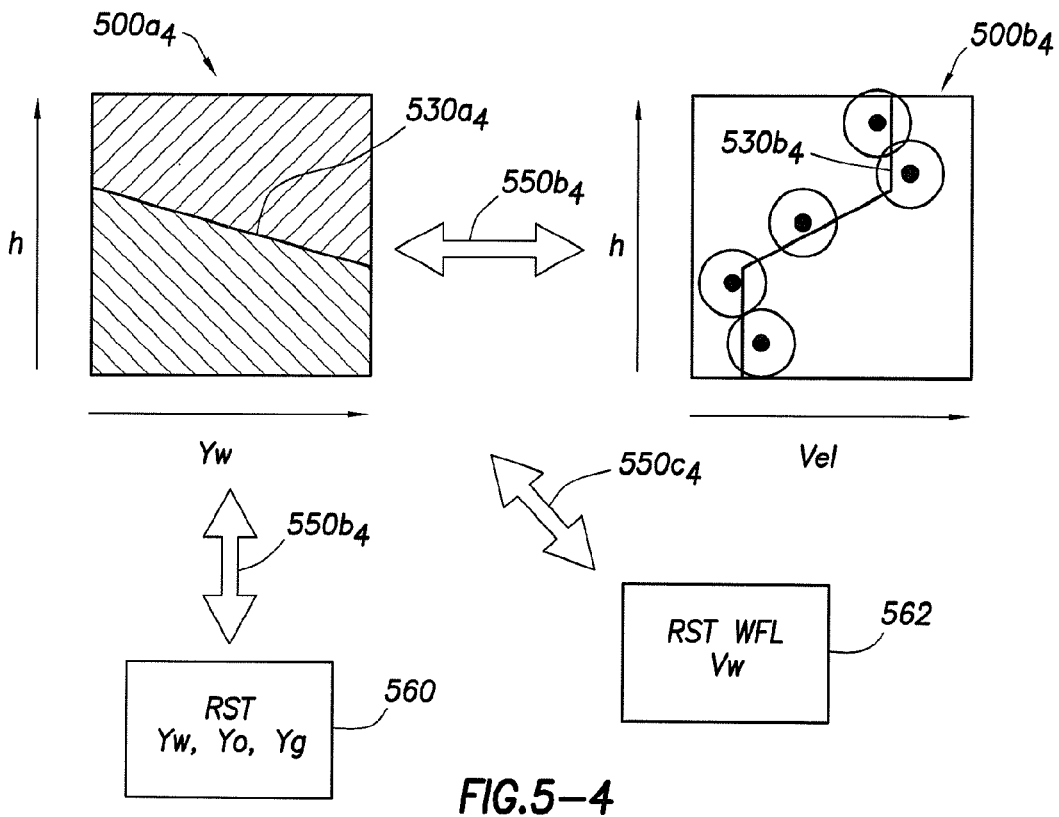

FIG. 3-4 is a chart 300a' showing a fitted curve holdup profile 330a' applied to the holdup profile 330a of FIG. 3-1. The chart 300a' plots the fitted curve holdup profile 330a' based from +r,−r (y-axis) versus Yw(x) (x-axis). FIG. 3-5 is a chart 300b' showing a fitted curve velocity profile 330b' applied to the velocity profile 330b set of FIG. 3-2. The chart 300b' plots the fitted curve velocity profile 330b' based from +r,-r (y-axis) versus V(x) (x-axis).

FIG. 3-5 shows another view of the cross section of the pipe 310 depicting a diameter x and a radius r with a chord at $2\sqrt{r^2-x^2}$. The fluid flow rate ($Q_w$) can be expressed as an integral, rather than a summation as in Eq. 1:

$$Q_w = \int_{-r}^{+r} Y_w(x) \cdot v(x) \cdot 2\sqrt{(r^2-x^2)} dx \qquad \text{Eq. 3}$$

where $Q_w$ is the water flow rate; $Yw_n$ is the water holdup for the n'th layer; x is the diameter of the pipe; v(x) is the fluid velocity; and r is the radius of the pipe in the wellbore.

In Eq. 3, the water flow rate $Q_w$ may represent a water flow rate, if other phases are also present. When other phases are also present, an analogous integral applies to the other phases as well, and Eq. 3 may be rewritten generically as:

$$Q_n = \int_{-r}^{+r} Y_n(x) \cdot v(x) \cdot 2\sqrt{(r^2-x^2)} dx \qquad \text{Eq. 4}$$

where $Q_n$ is the flow rate of water, oil or gas; $Y_n$ represents holdup for the n'th layer; and r is the radius of the pipe in the wellbore.

The holdup and the velocity curves curve fitted independently may provide a given accuracy for each curve. When the holdup and velocity curves are curve fitted in light of one another, they may combine information to generate a combined result. A curve with a shape mutual to both data sets may be applied to generate a result common to both. Since the holdup curve is a near mirror image 330a to the velocity curve 330b, the curves may be fitted to align to both curves. As shown in FIGS. 3-1 and 3-2, the holdup profile 330a and the velocity profile 330b may be symmetric or identical when arranged side-by-side and the two curves are scaled together.

Referring now to FIGS. 4-1 and 4-2, two profiles that are symmetric about a vertical axis, but with scales in horizontal axes that are different, are depicted. The vertical axes in FIGS. 4-1, 4-2, and 4-3 are dimensionless heights in a pipe from bottom to top (or vertical pipe diameters), ranging from 0 to 1, where 0 indicates the bottom of the pipe, and 1 indicates the top of the pipe. In FIG. 4-1, water hold up is on the horizontal axis, and a holdup profile 430a is plotted with a range of 0 to 1 along the vertical axis. With the increase in vertical height in the pipe from bottom to top, the water holdup decreases from 1 to 0.

FIG. 4-2 is the same as FIG. 401, except that the horizontal axis is the velocity and a velocity profile 430b is generated. The velocity may have a range of about 0.00 ft/min (0.00 m/s) to about 400.00 ft/min (i.e. 2.03 m/s). With an increase in vertical height in the pipe from bottom to top, the velocity increases from about less than 100 ft/min (i.e. 0.51 m/s) to about 400 ft/min (i.e. 2.03 m/s). In the example for FIGS. 4-1 and 4-2, the gain is negative. In the example embodiment shown in FIG. 4-1, holdup data are fitted with a hyperbolic tangent curve; in FIG. 4-2, velocity data are fitted with a hyperbolic tangent curve with the same shape with a negative gain and an offset.

For purposes of this disclosure, the first and second functions fitted for the holdup measurements and the velocity measurements are considered the same or similar as long as they have the same mathematical behavior, or shape, within their ranges, i.e. for dimensionless height in a pipe within [0, 1]. For computational efficiency, the two functions may not be expressed in identical polynomials, or a particular function or a series of functions. The two functions may be considered, for purposes herein, to be the same or similar as long as the error between them is not greater than the curve fitting errors.

In an embodiment, the order of the curve fitting may be irrelevant: either of the two data sets, the holdup data set or velocity data set can be fitted first, then using the resulting curve to fit the other data set. For example, in an embodiment, the holdup curve may be fitted first, then the holdup curve can be used to fit the velocity data set. In another embodiment, the fitting order is reversed, i.e. the velocity data set may be fitted first, then the velocity curve can be used to fit a holdup data set. In yet another embodiment, a same curve may be fitted to both holdup data and velocity data simultaneously.

The fitting errors for both curves can be summed together as a total error and the curve fitting algorithm may iterate (once or more than once) to minimize the total error until the total error reaches a minimum or a desired level.

The curve fitting of the velocity data can also take into account data not measured but inferred by Prandtl's law. According to Prandtl's law, the velocity at any point in the cross-section of a conduit will vary with the distance from the center of the conduit and a power law, which can be expressed as:

$$v(r) = v_{max}\left[1 - \frac{r}{R}\right] \qquad \text{Eq. 5}$$

where v(r) is the velocity at a distance r from the center of the conduit, $v_{max}$ is the velocity at the centerline of the pipe, R is the radius of the conduit and m is an exponent that may be taken as $\frac{1}{7}$.

The fluid velocity at a wall, based on Prandtl's law is assumed to be zero. The velocity profile 430b may be refined such that the velocity profile follows Prandtl's law based on flow characteristics at the pipe wall. For x=1 (i.e. at the top wall) and x=0 (i.e. at the bottom wall), the velocity may be 0. FIG. 4-3 shows another velocity profile 430b' based on the velocity profile 430b in FIG. 4-2, but with added refinement following the Prandtl's one-seventh law near the pipe walls (i.e. when x=1 and 0). FIG. 4-3 shows the velocity profile refinement at the top and bottom walls, or in other words, along the vertical axis of a pipe. For the velocity at other parts of the cylindrical wall, the same velocity profile refinement may be applied. The Prandtl refinement may reduce the flow rate of thin high side or low side layers of oil or water.

In an embodiment, the size of a measurement probe/sensor (e.g., probes 131a,b of FIGS. 1 and 2) may affect the measurement. In an embodiment, an optical or electrical holdup probe is generally small enough relative to the size of the conduit as to have negligible effect on the flow. For this reason, holdup measurements can be considered as if the probe were a point probe.

In an embodiment, a spinner flow meter (e.g., 137 of FIG. 1) may have a sweeping diameter up to about 1" (2.54 cm). In some cases, the spinner flow meter may not be considered as a point probe due to its size relative to the size of the conduit or wellbore. Thus, the measurement from a spinner flow meter may be considered as a measurement of the average velocity within the area occupied by the spinner blades. The fitted velocity profile can be treated as an average of the point velocity field (or a modified velocity profile), and the modified velocity profile may be extrapolated from the fitted velocity profile.

The modified velocity profile can be used instead of the fitted velocity profile wherever a velocity profiled is used, as discussed in this disclosure. For details regarding mini-spinner velocity averaging and the related effects on velocity profiles, flow rates etc., see U.S. Provisional Application No. 61/447,174, filed Feb. 28, 2011, and U.S. Application titled "METHODS AND SYSTEMS FOR INTERPRETING MULTIPHASE FLUID FLOW IN A CONDUIT" and filed Dec. 4, 2011 with Ser. No 13/310,788.

In an embodiment, the curve fitted to the holdup data may map directly to the velocity profiles when a combination of the MAPFLO™ profiles multiplied by the Prandtl one seventh power monophasic velocity profiles is used. Once the velocity profiles and holdup profile are obtained using any one of the above discussed methods, the determination of flow rates may be based on Eq. 3 or similar equations. The velocity profiles, holdup profiles and the flow rates may be further used for other purposes in an oil production operation, as would be readily recognized by one of ordinary skill in the field of production logging.

The relationship between the water holdup and velocity profile can be used, for example, to adjust the fitted curves for the holdup and velocity data sets. This relationship of the two curves can also be used in many other ways. FIGS. 5-1 through 5-4 show examples of ways in which the two curves can be used. In each of these figures, a plot 500$a_{1-4}$ of a holdup profile 530$a_{1-4}$ is shown on the left and a plot 500$b_{1-4}$ of a velocity profile 530$b_{1-4}$ is shown right with an arrow depicting interaction 550$a_{1-4}$, 550$b_{3-4}$, and/or 550$c_4$ therebetween. The interaction may be a one or two way interaction involving interpretation using, for example MAPFLO™, to interpret (e.g., curve fit or account for missing or corrupt data).

When one of the two types of data (e.g. velocity data) is not available or incomplete due to faulty or low quality measurements for a certain depth or a certain well, then such data can be estimated indirectly from the other dataset (e.g. from the holdup data) since the same shaped curve is used for both. For example, in the presence of a complete profile of holdup data but incomplete or error-filled spinner velocity data, the holdup profile 530$a_1$ can be applied to incomplete or error-ridden velocity data, as illustrated in FIG. 5-1. In a reverse case, where usable holdup data has not been acquired, the spinner velocity profile 550$b_1$ (and/or velocity data) can be used to create a holdup profile by applying the same curve fit thereto.

In the presence of complete holdup data and velocity data of sufficient quality (within error thresholds), an average curve can be fitted to the holdup profile 530$a_2$ and the spinner velocity profile 530$b_2$ (and/or velocity data) to minimize curve fitting error as illustrated in FIG. 5-2.

In some embodiments, the holdup profile and velocity profile may describe the local fluid properties in a well, and may be generated from individual local measurements obtained by tools (as noted above) containing various sensors for such purposes. The methods described in this application may also be used to obtain profiles using with fewer individual local measurements.

In an embodiment, individual velocity measurements may be combined with pipe averaged holdup measurements and converted into a synthetic holdup profile 530$a_3$ for subsequent processing (FIG. 5-3). The various measurements (e.g., pipe averaged holdup measurements, $Y_w$, $Y_o$, $Y_g$) can be obtained from currently commercially available downhole tools, e.g. a pulsed-neutron gamma ray-energy discriminating logging tool. The assignee SCHLUMBERGER™ manufactures one such tool, called RESERVOIR SATURATION TOOL™, or RST™. A pulsed-neutron gamma ray energy discriminating logging tool can provide a pipe averaged holdup measurement. The pipe averaged holdup measurement may be sufficient standing alone to determine the gain/offset in fitting the holdup profile 530$a_3$ based on spinner velocity profile.

In some embodiments, when a large number data points are available, e.g. when a complete set of velocity data and at least a partial set of holdup and water velocity data are available, a curve can be created from both the holdup and velocity data and an average curve may be used as the profile for both the holdup profile and the velocity profile. Further, the holdup curve may be a weighted average of the holdup measurements from two different types of downhole tools 560, 562 (such as an RST™ measurement and an FSI™ measurement, for example) in addition to the probe holdups, while the combination of the holdup and spinner data can be used to generate a velocity profile that may be compared with and modified by the RST water velocity ($V_w$). FIG. 5-4 illustrates one such situation.

Another use of the relationship between holdup measurements and velocity measurements is to validate data sets. When no curve can fit both datasets (i.e. holdup data and velocity data) within a certain curve fitting error threshold, the lack of a fitted curve can indicate some data points have problems. When the total error is above the curve fitting error threshold, further investigation into the data sets may be used to identify and locate the problems, which could be related to the operation of the tool used to obtain the measurements, or corruption to the storage device for the measurements, or the like. In an embodiment, the two sets of measurements may be rejected. When the total error is equal to or less than the threshold, the two sets of measurements and the two fitted curves are validated. As such, a mutually shaped fitted curve for both data sets can be used as a measure for data quality analysis and control. The interpretation techniques described herein can be implemented in the stable intervals between producing intervals.

Figure 6:
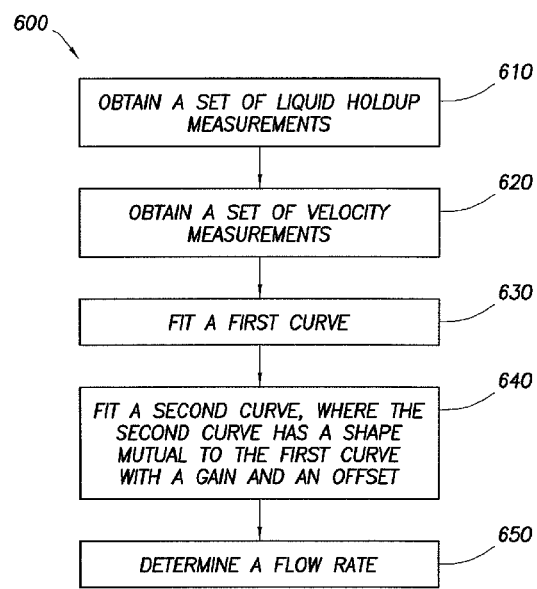
Figure 7:
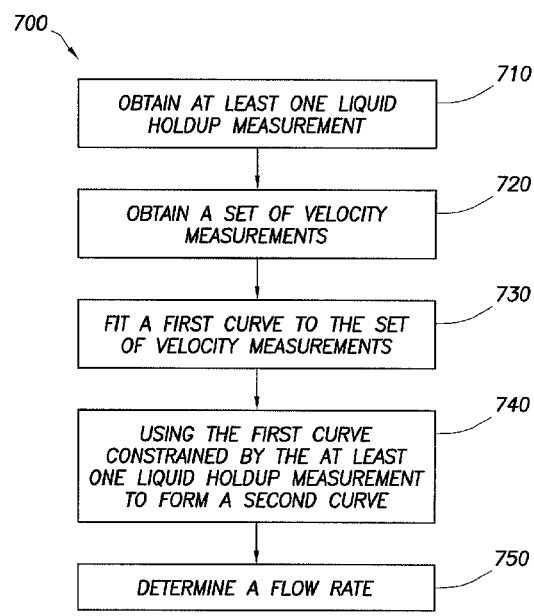
FIG. 7 is a flow diagram of another example method of interpreting measurements of a multi-phase fluid flow in a conduit.
Figure 8:
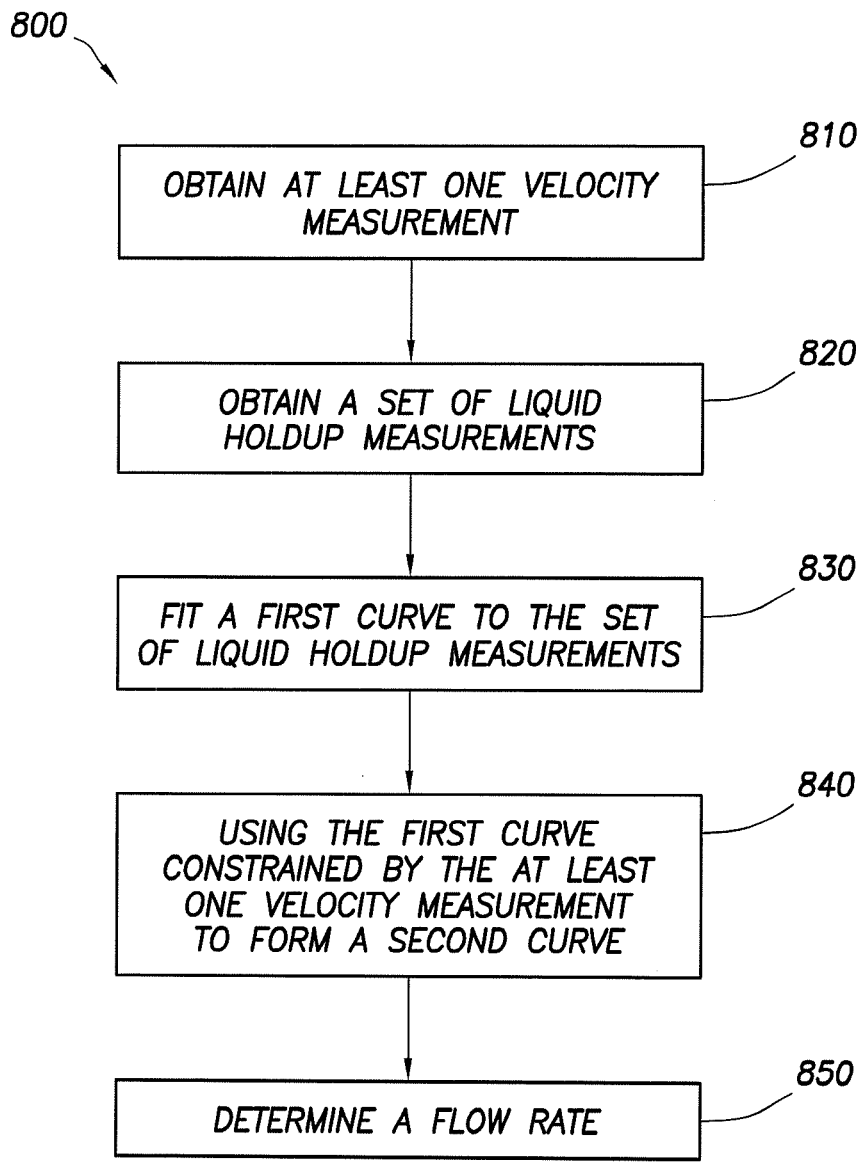
FIG. 8 is a flow diagram of yet another example method of interpreting measurements of a multi-phase fluid flow in a conduit.

Turning now to FIGS. 6, 7 and 8, various methods 600, 700 and 800 to interpret measurements of a multi-phase fluid flow in a conduit are presented. The method 600 of FIG. 6 begins with obtaining 610 a set of fluid holdup measurements. The set of fluid holdup measurements may be obtained using a downhole tool, such as FSI™, or an RST™ as described above. The number of measurements to complete a set may depend on what type of downhole tool is being used. For example, for the FSI™ tool, six local water holdup measurements and six local gas holdup measurements may be obtained in each logging pass. For RST™, a logging pass may include one measurement of water, gas and oil holdup. For other tools, such as a Flow-Caliper Imaging Sonde referred to as PFCS™ or a Digital Entry and Fluid Imager Tool referred to as DEFT™, four local water holdup measurements may be obtained. With a gas holdup optical sensor tool referred to as GHOST™ tool, four local gas holdup measurements may be obtained. Any other downhole tool capable of measuring holdup and velocity can be used as well.

The method 600 also involves obtaining 620 a set of velocity measurements, fitting 630 a first curve to one of the sets of measurements, and fitting 640 a second curve to the other set of measurements. The second curve has a mutual shape to the first shape, however with a different gain and offset. The curve fitting may be performed according to various curve fitting algorithms, including least squares fit, Levenberg-Marquardt, and the like, and performed using various commercially available software programs.

In one embodiment, the first curve is fitted at 630 to holdup measurements to produce a holdup profile, and then the second curve having a mutual shape is fitted at 640 to the velocity measurements to produce a velocity profile. In an embodiment, the order can be reversed, such that the first curve is fitted at 630 to the velocity measurements to produce the velocity profile, and then the second curve having a mutual shape is fitted at 640 to the holdup measurements to produce the holdup profile. In still another embodiment, the fitting at 630 and 640 can occur simultaneously. The method 600 may also involve determining 650 a flow rate. The flow rate may be determined based on a mathematical equation (such as Eq. 3 defined above), and the holdup profile and velocity profile.

Turning now to FIG. 7, the method 700 begins with obtaining 710 at least one fluid holdup measurement. The holdup measurement(s) may be a pipe averaged holdup measurement as described above. In an embodiment, 710 may include obtaining a plurality of fluid holdup measurements, some of which may be in error. The method 700 may also involve obtaining 720 a set of velocity measurements, fitting 730 a first curve to the set of velocity measurements as a velocity profile, and using 740 the first curve constrained by the fluid holdup measurement(s) to produce a second curve (which is the first curve with a gain and an offset) as a holdup profile. The method 700 may also involve determining 750 flow rate as previously described with respect to 650.

Turning now to FIG. 8, the method 800 begins with obtaining 810 at least one velocity measurement. In an embodiment, 810 may involve obtaining a plurality of velocity measurements, some of which are in error. The method 800 may also involve obtaining 820 a set of fluid holdup measurements, fitting 830 a first curve to the set of fluid holdup measurements as a fluid holdup profile, and using 840 the first curve constrained by the at least one fluid holdup measurement to produce a second curve (which is the first curve with a gain and an offset) as a velocity profile. The method 800 may also involve determining 850 flow rate as previously described with respect to 650.

As those with skill in the art will understand, one or more of the parts of methods discussed above may be combined and/or the order of some operations may be changed. Further, some operations in methods may be combined with aspects of other example embodiments disclosed herein, and/or the order of some operations may be changed. The process of measurement, its interpretation and actions taken by operators may be done in an iterative fashion; this concept is applicable to the methods discussed herein.

Figure 9:
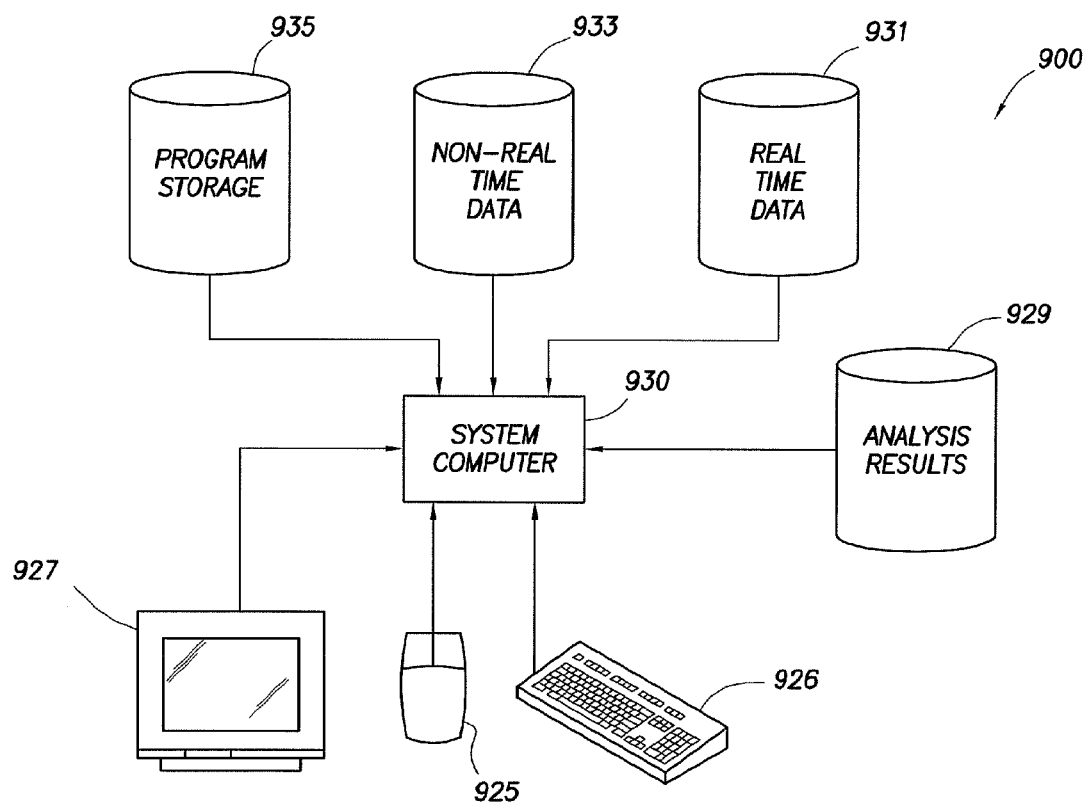
FIG. 9 shows a computer system by which the methods can be implemented.

Portions of methods may be performed by any suitable techniques, including on an automated or semi-automated basis on computing system 900 in FIG. 9. An example computer system 900 is shown in FIG. 9. The computer system 900 includes a computer 930 in communication with disk storage devices 929, 931, 933 and 935, which may be external hard disk storage devices and measurement sensors (not shown). It is contemplated that disk storage devices 929, 931, 933 and 935 may be conventional hard disk drives and, as such, may be implemented by way of a local area network or by remote access. While disk storage devices are illustrated as separate devices, a single disk storage device may be used to store the program instructions, measurement data, and results as desired.

In one implementation, petroleum real-time data from the sensors may be stored in disk storage device 931. Various non-real-time data from different sources may be stored in disk storage device 933. The system computer 930 may retrieve the appropriate data from the disk storage devices 931 or 933 to process data according to program instructions that correspond to implementations of various techniques described herein. The program instructions may be written in a computer programming language, such as C++, Java and the like. The program instructions may be stored in a computer-readable medium, such as program disk storage device 935. Such computer-readable media may include computer storage media. Computer storage media may include volatile and non-volatile, and removable and non-removable media implemented in any method or technology for storage of information, such as computer-readable instructions, data structures, program modules or other data. Computer storage media may further include RAM, ROM, erasable programmable read-only memory (EPROM), electrically erasable programmable read-only memory (EEPROM), flash memory or other solid state memory technology, CD-ROM, digital versatile disks (DVD), or other optical storage, magnetic cassettes, magnetic tape, magnetic disk storage or other magnetic storage devices, or any other medium which can be used to store the desired information and which can be accessed by the system computer 930. Combinations of any of the above may also be included within the scope of computer readable media.

In one implementation, the system computer 930 may present outputs primarily onto graphics display 927, or via a printer (not shown). The system computer 930 may store the results of the methods described above on disk storage 929, for later use and further analysis. The keyboard 926 and the pointing device (e.g., a mouse, trackball, or the like) 925 may be provided with the system computer 930 to enable interactive operation.

The system computer 930 may be located on-site near the well or at a data center remote from the field. The system computer 930 may be in communication with equipment on site to receive data of various measurements. Such data, after conventional formatting and other initial processing, may be stored by the system computer 930 as digital data in the disk storage 931 or 933 for subsequent retrieval and processing in the manner described above. While FIG. 9 illustrates the disk storage, e.g. 931 as directly connected to the system computer 930, it is also contemplated that the disk storage device may be accessible through a local area network or by remote access. Furthermore, while disk storage devices 929, 931 are illustrated as separate devices for storing input petroleum data and analysis results, the disk storage devices 929, 931 may be implemented within a single disk drive (either together with or separately from program disk storage device 933), or in any other conventional manner as will be fully understood by one of skill in the art having reference to this specification.

While the disclosure has been disclosed with respect to a limited number of embodiments, those skilled in the art, having the benefit of this disclosure, will appreciate numerous modifications and variations therefrom. While the disclosure has been described in the context of applications in downhole tools, the apparatus of the disclosure can be used in many applications requiring shear velocity evaluation of a medium.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed:

1. A method for interpreting measurements of a multi-phase fluid flow in a conduit, the method comprising:
   obtaining a set of holdup measurements from a holdup sensor;
   obtaining a set of velocity measurements from a flow velocity sensor;
   using one or more processors, fitting a first curve to a first set of the holdup measurements and a first set of velocity measurements; and
   using one or more processors, fitting a second curve to a second set of holdup measurements and a second set of velocity measurements, wherein the second curve comprises a shape mutual to the first curve with an independent gain and an independent offset; and
   determining a flow rate for one phase of the multi-phase fluid flow based on the first and second curves.

2. The method of claim 1,
   wherein the first set is the set of holdup measurements and the second set is the set of velocity measurements; and
   wherein the first curve is a holdup profile and the second curve is a velocity profile.

3. The method of claim 1, wherein the first curve comprises one of a function with a linear fit to the measurements; a function with spline interpolations; and a function with spline interpolations and a constant projection.

4. The method of claim 1, wherein the first curve comprises a hyperbolic tangent curve with at least two adjustable curve-fitting coefficients.

5. The method of claim 1, further comprising:
   modifying one of the first and second curves that is fitted to the velocity measurements according to Prandtl's law at a wall of the conduit, wherein the modified curve comprises a velocity profile.

6. The method of claim 1, further comprising:
   modifying one of the first and second curves that is fitted to the set of velocity measurements based on an averaging effect of the velocity measurements, wherein the modified curve is a modified velocity profile; and
   generating a fluid flow rate with a holdup profile and the modified velocity profile.

7. The method of claim 1, further comprising:
   generating a first curve-fitting error for the first curve;
   generating a second curve-fitting error for the second curve;
   generating a total curve-fitting error as a sum of the first and second curve-fitting errors; and
   rejecting the set of holdup measurements and the set of velocity measurements when the total curve-fitting error is above a threshold.

8. The method of claim 7, further comprising:
   validating the set of holdup measurements and the set of velocity measurements when the total curve-fitting error is equal to or below the threshold; and
   adjusting at least one curve-fitting parameter of the first curve and the second curve to minimize the total curve-fitting error.

9. The method of claim 1, wherein the conduit comprises a pipe in an oilfield wellbore.

10. A method for interpreting measurements of a multi-phase fluid flow in a conduit, comprising:
    obtaining at least one fluid holdup measurement from a holdup sensor;
    obtaining a set of velocity measurements from a flow velocity sensor;
    using one or more processors, fitting a first curve to the set of velocity measurements as the velocity profile;
    using the first curve constrained by the at least one fluid holdup measurement to form a second curve as the fluid holdup profile; and
    determining a flow rate for one phase of the multi-phase fluid flow based on the first and second curves.

11. The method of claim 10,
    wherein the at least one fluid holdup measurement is one of a pipe average holdup measurement and a local probe holdup measurement.

12. The method of claim 11,
    wherein the pipe average holdup measurement is obtained from a pulsed-neutron gamma ray-energy discriminating logging tool.

13. A method for interpreting measurements of a multi-phase fluid flow in a conduit, comprising:
    obtaining at least one velocity measurement from a holdup sensor;
    obtaining a set of fluid holdup measurements from a flow velocity sensor;
    using one or more processors, fitting a first curve to the set of fluid holdup measurements as the fluid holdup profile;
    using the first curve constrained by the at least one velocity measurement to form a second curve as the velocity profile; and
    determining a flow rate for one phase of the multi-phase fluid flow based on the first and second curves.

14. The method of claim 13, wherein the at least one velocity measurement is one of a pipe average velocity measurement and a local velocity measurement.

15. A system for interpreting measurements of a multi-phase fluid flow in a conduit, the apparatus comprising:
    a holdup sensor to obtain a set of fluid holdup measurements;
    a flow velocity sensor to obtain a set of velocity measurements;
    a processor in electronic communication with the holdup sensor and the flow velocity sensor, the processor fitting a first curve to a first set of fluid holdup measurements a first set of velocity measurements and fitting a second curve to a second set of the fluid holdup measurements or a second set of the velocity measurements, wherein the second curve is fitted using the first curve constrained by at least one of the second set of fluid holdup measurements or the second set of velocity measurements, and wherein the first curve and the second curve comprise a fluid holdup profile and a velocity profile.

16. The system of claim 15, wherein the second curve has a same shape of the first curve with an independent gain and an independent offset and wherein the first curve and the second curve comprise a fluid holdup profile and a velocity profile.

17. The system of claim 15, wherein the first curve is a hyperbolic tangent curve with two adjustable curve-fitting coefficients.

18. The system of claim 15, wherein the holdup sensor and the flow velocity sensor are disposed about a downhole tool configured to move inside the conduit.

19. The system of claim 15, wherein the processor comprises a computer readable data storage in electronic communication with the processor that stores the set of fluid holdup measurements and the set of velocity measurements.

20. The system of claim 19, wherein the computer readable data storage further comprises computer executable instructions that, when executed by the processor, causes the processor to compute a fluid flow rate in the conduit.

21. The system of claim 19, wherein the computer readable data storage further comprises computer executable instructions that, when executed by the processor, causes the processor to constrain a fluid holdup profile by one measurement of the set of velocity measurements.

22. The system of claim 19, wherein the computer readable data storage further comprises computer executable instructions that, when executed by the processor, cause the processor to constrain a velocity profile by one measurement of the set of fluid holdup measurements.

23. The system of claim 19, wherein the computer readable data storage further comprises computer executable instructions that, when executed by the processor, cause the processor to:
    compute a total curve-fitting error as a function of a first curve-fitting error for the first curve and a second curve-fitting error for the second curve; and
    reject the set of velocity measurements and the set of fluid holdup measurements when the total curve-fitting error exceeds a threshold.

\* \* \* \* \*